United States Patent
Curtis

(10) Patent No.: US 9,091,582 B2
(45) Date of Patent: Jul. 28, 2015

(54) VERTICAL AND HORIZONTAL BEAM HYBRID PIPETTE CALIBRATION SYSTEM

(71) Applicant: Artel, Inc., Westbrook, ME (US)

(72) Inventor: Richard H. Curtis, Gorham, ME (US)

(73) Assignee: Artel, Inc., Westbrook, ME (US)

( * ) Notice: Subject to any disclaimer, the term of this patent is extended or adjusted under 35 U.S.C. 154(b) by 0 days.

(21) Appl. No.: 13/941,102

(22) Filed: Jul. 12, 2013

(65) Prior Publication Data

US 2014/0016129 A1    Jan. 16, 2014

Related U.S. Application Data

(60) Provisional application No. 61/671,447, filed on Jul. 13, 2012.

(51) Int. Cl.
  *G01N 21/00* (2006.01)
  *G01F 22/00* (2006.01)
  *G01F 25/00* (2006.01)

(52) U.S. Cl.
  CPC ............ *G01F 22/00* (2013.01); *G01F 25/0084* (2013.01); *G01N 21/00* (2013.01)

(58) Field of Classification Search
  USPC .................. 356/432–444, 418–419, 319–320; 250/334, 344, 339.05; 436/8, 18; 422/922
  See application file for complete search history.

(56) References Cited

U.S. PATENT DOCUMENTS

| | | | |
|---|---|---|---|
| 3,622,795 A | 11/1971 | Dorman, Jr. et al. | |
| 5,183,761 A * | 2/1993 | Freeman et al. | 436/8 |
| 5,298,978 A | 3/1994 | Curtis et al. | |
| 5,492,673 A | 2/1996 | Curtis et al. | |
| 6,404,501 B1 * | 6/2002 | Hafeman et al. | 356/436 |
| 6,496,260 B1 * | 12/2002 | Hafeman et al. | 356/433 |
| 6,741,365 B2 | 5/2004 | Curtis | |
| 6,995,844 B2 * | 2/2006 | Hafeman et al. | 356/433 |
| 7,061,608 B2 | 6/2006 | Bradshaw et al. | |
| 7,187,455 B2 | 3/2007 | Curtis | |
| 7,640,787 B2 | 1/2010 | Curtis et al. | |
| 7,772,008 B2 | 8/2010 | Curtis et al. | |
| 7,791,716 B2 | 9/2010 | McNally et al. | |
| 7,870,797 B2 | 1/2011 | Curtis et al. | |

(Continued)

OTHER PUBLICATIONS

International Search Report and Written Opinion in corresponding PCT application No. PCT/US2013/050332, Dec. 13, 2013, 11 pp.

*Primary Examiner* — Hoa Pham
(74) *Attorney, Agent, or Firm* — Caseiro Burke LLC; Chris A. Caseiro

(57) ABSTRACT

A system and related method for determining the volume of a sample solution delivered by a liquid delivery device. The system includes devices for adding and removing diluent, the sample solution under analysis and a mixture of the two in a cell having a substantially constant cross sectional area and a known horizontal optical path length. The system includes one or more spectrophotometers to measure horizontally and vertically absorbance associated with two distinct chromophores. A first chromophore of unknown concentration is in the diluent and a second chromophore of known concentration is in the sample solution. The method determines absorbance horizontally and vertically of the first chromophore prior to adding the sample solution and then determining absorbance of the first chromophore horizontally and vertically and the second chromophore horizontally after mixing the diluent and sample solution together. That information is used to determine the volume of the sample solution added to the cell.

16 Claims, 1 Drawing Sheet

(56) References Cited

U.S. PATENT DOCUMENTS

| | | |
|---|---|---|
| 7,919,327 B2 | 4/2011 | Bradshaw et al. |
| 7,998,747 B2 | 8/2011 | Bradshaw et al. |
| 8,003,405 B2 | 8/2011 | Albert et al. |
| 8,096,197 B2 | 1/2012 | Curtis et al. |
| 8,404,158 B2 | 3/2013 | Curtis et al. |
| 2004/0246501 A1* | 12/2004 | Curtis .................. 356/627 |
| 2009/0251681 A1 | 10/2009 | McNally et al. |
| 2013/0038873 A1 | 2/2013 | Curtis et al. |

* cited by examiner

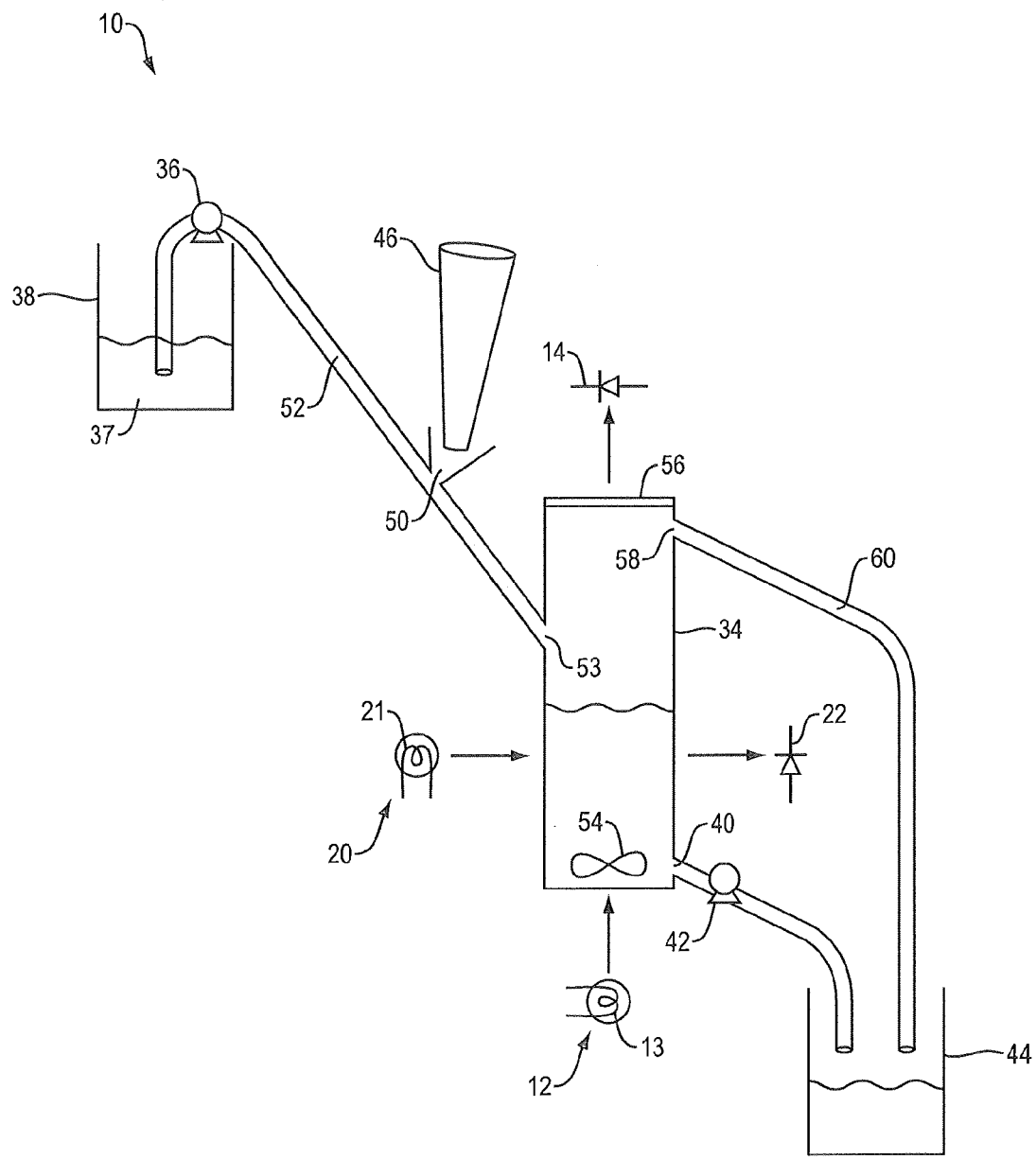

VERTICAL AND HORIZONTAL BEAM HYBRID PIPETTE CALIBRATION SYSTEM

CROSS REFERENCE TO RELATED APPLICATION

The present invention is a nonprovisional application, and claims the priority benefit of, U.S. provisional patent application Ser. No. 61/671,447, filed Jul. 13, 2012, entitled "VERTICAL BEAM CALIBRATION SYSTEM WITH HYBRID MULTI-WAVELENGTH FLOW CELL DESIGN" and assigned to a common assignee. The content of the priority application is incorporated herein by reference.

BACKGROUND OF THE INVENTION

1. Field of the Invention

The present invention relates to the measurement of liquid volumes using spectrophotometers. More particularly, the present invention relates to systems and related methods to test or calibrate liquid delivery devices using a combination of vertical spectrophotometry and horizontal spectrophotometry.

2. Description of the Prior Art

All currently manufactured colorimetric systems for testing or calibrating liquid delivery devices (e.g., the PCS® system and the MVS® system, both offered by Artel, Inc. of Westbrook, Me., assignee of the present invention and application, and the Pipette Volume Calibration Kit offered by VistaLab of Mt. Kisco, N.Y.) use a multiplicity of sample solutions for the purpose of testing a wide range of deliverable solution volumes. The sample solution is delivered by the device being tested into a diluent in a measurement vessel, and the solutions are mixed before measuring the absorbance of the resulting mixture. A concentrated sample solution is used to test a small liquid delivery volume, and a more dilute sample solution is used to test a large liquid delivery volume. As used herein, a "vessel" is any vial, cell, bottle, microtiter plate or other type of container for retaining a fluid therein, whether such vessel is sealed or not. Also, the vessel may be designed for collecting optical absorbance measurements by use of a horizontal beam spectrophotometer (such as a conventional UV-Vis spectrophotometer like the Cary 5000, Varian, Inc., Palo Alto, Calif.) or a vertical beam spectrophotometer (such as a microtiter plate reader like the ELx800, BioTek Instruments, Winooski, Vt.).

The Artel PCS is a photometric method and system for calibration of pipettes or other liquid delivery systems. Its advantages are highly accurate and reproducible measurement results which are traceable to national standards, simplicity of use, independence from environmental factors such as vibrations, temperature variations, and drafts, and applicability to very low (microliter) liquid dispense volumes. Its disadvantages are relatively high cost of consumables, since the diluent solution is packaged in a clear disposable vial which needs to be manufactured to high optical standards, and the need for operator intervention to change to a fresh vial of diluent after a certain number of sample additions (between 11 and 40 dispenses, depending on the sample size and concentration). One important element in achieving the high degree of accuracy and precision of the Artel PCS is the use of a horizontal beam spectrophotometer which measures absorbance at two wavelengths and which has extremely low noise and high accuracy (noise typically better than $2 \times 10^{-5}$ absorbance units at an absorbance of 1).

The Artel MVS is a photometric measurement method and system for calibration of multichannel pipettes and automated liquid delivery devices. It is based on a specialized microtiter plate to which both diluent and sample solutions are added. It employs a vertical beam spectrophotometric system to measure absorbance at two wavelengths. The volume of sample solution can be calculated knowing the dimensions of the wells in the microtiter plate and measured absorbances. Its advantages are: adaptability to measuring delivery volume from multichannel dispensers (up to 384 dispenses at once), speed, results which are traceable to national standards, and independence from operator technique or environmental variables. Its weaknesses are high consumable costs (primarily for the specialized microtiter plate), and a limitation that only one sample volume can be delivered per well of the microtiter plate.

Many applications, such as the automated testing of liquid delivery devices, are preferably done automatically, without operator intervention. It should be possible to schedule and carry out testing operations throughout the day on an automated basis with no operator attention or intervention. Neither of the above described existing-art methods fulfill this need, as both require operator intervention to change out the disposable vial or microtiter plate. For many critical applications in which it is important to verify liquid handler performance on a frequent basis, cost of consumables for either of the above methods becomes prohibitive. What is needed is a liquid delivery calibration system that does not require operator intervention and that has significantly lower consumables cost per test. What is also needed is a liquid delivery calibration system that minimizes the need for operator time and equipment time in the procedure.

SUMMARY OF THE INVENTION

It is an object of the present invention to provide a liquid delivery calibration system that does not require operator intervention and that has significantly lower consumables cost per test. It is also an object of the invention to provide a liquid delivery calibration system that minimizes the need for operator time and equipment time in the procedure. Further objects of the invention include: a) to provide a single system and method to cost effectively cover a volume range from 100 nl to 10 ml; b) reduced consumables cost; c) speed of operation should only be limited by the speed at which an operator or automated dispenser can pipette, with a target of 1 to 1.5 minutes for a 10 data point calibration; d) insensitive to environment including, for example, insensitive to ambient low frequency vibrations, drafts, temperature gradients, or voltage fluctuations; and e) conformance to ISO 8655 part 7 and the results must be traceable to international standards.

These and other objects are achieved with the present invention, which is a system including a spectrophotometer with both horizontal and vertical beams, a measurement cell with substantially constant cross sectional area, an optical quality bottom and an open top, a bulk supply of diluent, a pump to carry diluent into the cell, another pump to empty the cell, a waste solution container, and a way to mix the contents of the cell. The related method involves pipetting a sample solution containing chromophore into either the open top of the cell or into a channel leading to the cell, mixing the sample solution with diluent that has been delivered from the bulk supply to create a sample-diluent mixture, and measuring with the spectrophotometer absorbance both horizontally and vertically at one or more wavelengths. Based on the absorbance measurements, the cell dimensions, and the optical properties of the sample and diluent solutions, the volume of sample solution added to the cell is calculated based on application of the Beer Lambert Law. The system may also be configured for a multiplicity of cells, for instance to test 8 or 12 channel dispensers.

The present invention is distinct from the MVS and PCS technologies in several ways. In regard to the MVS system, it is noted that that is limited to vertical absorbance measurement only, for which the reproducibility of absorbance measurements is limited by the fact that the light beam enters or exits the liquid contents of the cell through a meniscus at the air-liquid interface. The exact location and shape of the meniscus is not exactly reproducible from one measurement to the next due to: a) impurities (e.g. dust or bits of grit which carry oil or surfactant) at the air-liquid or the liquid-solid interfaces, which can affect the meniscus shape locally; and b) motion of the meniscus due to small ambient vibrations, residual motion left over from mixing, or air motion. In that regard, it is noted that the larger the diameter of the measuring cell the greater the possibility for motion. Further, in the MVS system, the readings are not reproducible to better than about 0.0005 absorbance units due to these effects. For this reason, the MVS system is engineered to never measure differences in absorbance smaller than 0.250 absorbance units, to assure that the error due to non-reproducibility of absorbance readings is small enough not to materially affect the overall measurement uncertainty. This requirement for never allowing a change of less than 0.250 absorbance units per sample addition rules out the possibility of adding many samples to the same well, even if they are small volume samples. If one were to try, the absorbance would quickly go beyond the limit of measurability. At most, in the best case, the user may be able to add eight samples before the absorbance got to 2.0, which is a reasonable limit for accurate measurement. In the worst case the user could only add one sample to the well. This number of samples is less than optimum from the point of view of economy or speed of operation. By using the present invention in a horizontal beam configuration, these limitations associated with the MVS process are eliminated.

The present invention provides for inclusion in the sample solution of only one chromophore, one that is different from a chromophore of the diluent. The existing MVS patent covers the case in which the sample solution contains both a first chromophore (the one of the diluent) and a second chromophore. That difference is made possible in the present invention by using a cell having a substantially constant cross section. In the MVS process, it is necessary that the microtiter plate be clean and dry before starting. The present invention differs in that, by using a cell of substantially constant cross section, the cell contents may be emptied automatically into a reservoir and diluent added automatically from a bulk supply; thus, it adds an automation feature not available in MVS. As a result, residual amounts of solution (volume unknown) containing unknown amounts of both chromophores may be left in the cell after it is emptied (that is, it has not been completely cleaned and dried) without a negative impact or an accumulation of error as a possibility.

In the PCS method, the corresponding limit for the minimum allowed absorbance change is one-tenth of what it is for MVS, namely 0.025 absorbance units. This is possible because the beam does not have to pass through a liquid-air interface, and the absorbance measurements are much more reproducible. For PCS, the absorbance readings at A=1 are reproducible within 0.000025 absorbance units, or twenty times as reproducible as for MVS, and this allows as many as 40 samples into each vial. The system of the present invention allows for selection of the concentration of the first chromophore, the one in the diluent, so that the vertical absorbance measurement at wavelength 1 is never less than about 1. This is the wavelength used for measuring total volume of liquid in the measurement cell. The uncertainty of 0.0005 absorbance units in this vertical measurement results in an overall uncertainty in the reported result of less than 0.1%, which is tolerable. In addition, the concentration of the second chromophore, the one in the sample solution, can be chosen so that the change of horizontal absorbance can be as little as 0.025 absorbance units, allowing many additions of sample solution before the solution becomes too concentrated to measure accurately. Following the example of PCS, the limit is probably on the order of 40 samples.

Thus, the system of the present invention utilizes elements of both the MVS and the PCS systems, in order to capture virtues of both systems into one unified system. The PCS aspect uses the horizontal absorbance measurement capability in order to allow many samples per filling of the measurement cell, resulting in fast and economic operation. The MVS aspect uses the ability of a vertical measurement system to measure total liquid volume in the measurement cell, meaning that the cell need not be prefilled with great accuracy at the factory, but can be filled in the field with an uncalibrated pump from a reservoir, allowing both economy of operation and the option for un-tended operation. These and other features and advantages of the invention will become more apparent upon review of the following detailed description, the accompanying drawings and the appended claims.

BRIEF DESCRIPTION OF THE DRAWING

The FIGURE is a simplified diagrammatic representation of the components of an embodiment of the present invention for carrying out the hybrid vertical beam-horizontal beam method of the present invention.

DETAILED DESCRIPTION OF A PREFERRED EMBODIMENT OF THE INVENTION

A hybrid calibration system 10 of the present invention is represented in the FIGURE. The system 10 includes a spectrophotometer subsystem including a vertical beam spectrophotometer 12 including a transmitter light source 13 and a detector 14. The spectrophotometer subsystem further includes a horizontal beam spectrophotometer 20 including a transmitter light source 21 and a detector 22. The spectrophotometer subsystem may be formed of a plurality of spectrophotometers including at least one horizontal beam spectrophotometer and one vertical beam spectrophotometer with a common computer processor for controlling light transmission and signal detection. Alternatively, the spectrophotometer subsystem may be established as a single spectrophotometer with transmitters and detectors suitable for carrying out horizontal beam and vertical beam spectrophotometry. Commercially available spectrophotometers, such as the S.I. Photonics 400 Series UV/Vis Spectrophotometer offered by S.I. Photonics, Inc. of Tucson, Ariz., could be used as either the vertical beam spectrophotometer 12 or the horizontal beam spectrophotometer 20, or both. Alternatively, the vertical beam spectrophotometer 12 and the horizontal beam spectrophotometer 20 could be assembled from various optical components and optical fibers commercially available from companies such as ThorLabs of Newton, N.J., or Ocean Optics of Dunedin, Fla. Conversely, the entire spectrophotometer subsystem could be designed and assembled from optics and optical components from companies such as Edmund Optics of Barrington, N.J. or Melles Griot of Carlsbad, Calif.

The system 10 further includes a fixed (non-disposable) open-top cylindrical cell 34, which is never completely filled with liquid. The volume of liquid contents in the cell 34 is related to the pathlength of light passing vertically through the cell 34. The cell 34 may stay in the system 10 for the life of the system 10, or it may be removable for ease of cleaning, storage etc. A device for filling the cell 34, such as a pump 36, which may be a computer-controlled pump, with an approximate volume of diluent 37 from a bulk diluent supply 38. There is no need to calibrate the pump 36, as the results provided by the system 10 are not sensitive to diluent volume. The cell 34 includes a drain port 40 and an associated drain pump 42 to enable a user of the system 10 to nearly empty the contents of the cell 34 into a waste container 44 at the conclusion of a measurement sequence. It is anticipated that an unknown volume of solution of unknown concentration will remain in the cell 34 after it is "emptied".

The system 10 also includes a sample solution delivery component 46, which may be a tip of a pipette, for example, or other conduit capable of delivering a sample solution and which can be removably engageable with a sample solution inlet port 50 of a diluent delivery conduit 52 for delivery of the diluent 37 to cell entry port 53. A mixing element 54 may form part of or be removably insertable into, the cell 34. Other designs that accomplish the same functions will be evident to people skilled in the art. The system 10 can also be configured with a number of cells configured in close proximity, so that a multichannel dispenser, either an automated liquid handler (ALH) or manual multichannel pipette can be tested by simultaneously delivering one channel per well.

The cell 34 may be an open topped flow cell with provision for emptying, filling, and mixing as noted. It may be circular in cross section with radius R; however the shape could also have any regular and uniform cross section. The cross sectional area of the cell 34 is denoted as $S_C$. Its value should be measured at the factory of its origin using a method traceable to national standards and that value may be stored, such as in memory or a database associated with a computer processor used to carry out calculations of the type described herein. The cell 34 is made of a material (e.g. borosilicate glass) which is known to be dimensionally stable, so the value of $S_C$ does not change over time. The pathlength of light passing horizontally thru the cell 34 is denoted as 1. This value may be measured at the factory of its origin using means traceable to national standards, and that value may also be stored in the manner indicated with respect to the cell's cross sectional area. It, too, should not change with time. Because the cell 34 is made of material known not to change size or shape over its lifetime the values of $S_C$ and 1 can be used to produce results traceable to national standards for the lifetime of the system 10 without need for re-measurement of these parameters. The cell 34 may have a cover 56, which may be automatically moved out of the light path when a reading is to be made, but otherwise is in place to stop liquid from splashing out of the cell 34 during mixing or transport. The cell 34 includes an overflow port 58 with overflow conduit 60 leading to waste container 44 so that the cell 34 cannot be completely filled, assuming the overflow port 58 is not blocked.

The system 10 may be used to carry out steps of a calibration method, a volume determination method, or both using results from horizontal beam spectroscopy and vertical beam spectroscopy on the contents of the cell 34. The method requires that a diameter of the cell 34 be chosen to allow rapid and thorough mixing of the contents therein, yet it must also have enough capacity to allow testing of delivery devices in the milliliter range. For an upper sample solution volume limit of 10 ml, these two requirements lead to a cell diameter of about two centimeters and a total capacity of 15 ml.

An example embodiment of the method of the present invention involves the use of two chromophores and absorbance measurements in both the horizontal and vertical directions at multiple wavelengths. This is only an example; other implementations will be evident to persons skilled in the art. In this example embodiment, the diluent 37 contains a first chromophore (e.g. such as a copper salt $CuCl_2$) with peak absorbance at $\lambda_1=730$ nm. Other chromophores are chosen so they do not absorb significantly at this wavelength. The sample solution to be used for calibration or volume determination includes a second chromophore, which may be a single chromophore or a combination of a plurality of chromophores, where the second chromophore has one or more features at wavelengths shorter than 730 nm. Examples for the single or combination second chromophore include Tartrazine and Ponceau S or a mixture of the two. The sample solution does not contain any of the first chromophore and the diluent 37 does not contain any of the second chromophore. Absorbances of the second or other chromophores can be measured at one or more wavelengths.

At some time before the calibration can begin, the photometer absorbances must be referenced to a baseline. The baseline readings relate zero at one wavelength to zero at another wavelength. Clear (non absorbent in the wavelength range of interest) "baseline" solution is added to the cell 34, and the cell 34 is rinsed adequately to assure that there is no chromophore left in the cell 34. Under these conditions, absorbance readings are taken at all wavelengths. These are the baseline absorbance values used for the measurement process. Since the baseline solution contains no chromophore, it has no absorbance, and thus the volume of baseline solution does not affect the results of either the horizontal or vertical absorbance measurements. The baseline measurement should be repeated periodically at intervals depending on the stability of the photometer. All absorbances in the analysis below are referred to the baseline value for that wavelength.

Diluent 37 in the diluent supply reservoir 38 contains the first chromophore. The pump 36 automatically moves an approximate amount of the diluent 37 into the cell 34 as dictated by the measurement sequence. As noted, it is not necessary for the volume delivery of the pump 36 to be either calibrated or highly reproducible. The FIGURE shows the addition of sample solution with a pipette tip as the sample delivery component 46; however, the delivery device can be anything which delivers liquid in a volume range that the cell 34 can accommodate. After an aliquot of sample solution is added to the cell 34, the diluent pump 36 delivers an aliquot of diluent 37, which is used to flush the entry area and conduit 52 and to assure that all of the sample solution makes it into the cell 34. The volume of this flushing diluent is $V_{flush}$. The exact volume is not critical to the results. The contents of the cell 34 are mixed after the sample and the flushing diluent have been added. The mixing element 54 may be a magnetic stir bar in the bottom of the cell 34, provided it is positioned within the cell 34 so that the vertical light beam does not contact it. As an alternative to a magnetic stir bar, the mixing element 54 may involve the use of diluent pump 36 or another pump device to establish a recirculation loop to recirculate the cell contents back into the cell entry port 53 of the cell 34, thereby mixing the contents in the process. The presence of a mixing mechanism (either one of them) will mean that the effective geometry of the cell 34 is not simply a right cylinder. The volume occupied by the stir bar (or by the recirculation loop), $V_{mix}$, needs to be taken into account in the calculations set out herein. $V_{mix}$ can be measured at the point of origin of the cell 34 and/or the system 10 and stored as noted.

After the sample solution is added to the cell 34 and mixed, absorbance of the contents of the cell 34 is measured both vertically and horizontally at the peak absorbance wavelength of the first chromophore. In the case of $CuCl_2$ that is 730 nm. These two absorbance values (vertical and horizontal) yield a value for the total volume of liquid in the cell 34, given the values of horizontal pathlength l, cell cross sectional area $S_C$ and mix volume $V_{mix}$. The concentration of the first chromophore is not important as long as it is enough to produce an absorbance in the most accurate range of the spectrophotometer subsystem 12. Detailed mathematical analysis is given below. The sample solution contains none of the first chromophore, but does contain the second chromophore with suitable concentration for measuring the volume of sample solution being delivered. Absorbance resulting from the presence of this second chromophore is measured horizontally at one or more wavelengths (e.g. for Ponceau S one wavelength may be 520 nm (peak), and another wavelength may be 420 nm (valley)). The following analysis treats only one wavelength, $\lambda_2$; however the same equations will pertain to other wavelengths where suitable features of the second chromophore are located. A feature is defined as a peak, or a valley or a plateau where the absorbance vs. wavelength curve is flat (zero slope or nearly so). The following description assumes that the sample solution contains only one chromophore, although as noted, a combination of chromophores may be added to the sample solution in order to create an absorbance profile which is optimum for a given application.

Prior to describing the calculations that may be performed and information obtained using the system 10, it is to be noted that the system 10 is readily adaptable into a multichannel version. The use of a channel rather than a pipette tip to deliver the sample to the cell 34 allows a relatively close spacing of the access points (9 mm), which is typical of multichannel pipettes and automated delivery devices, so the design shown in the FIGURE can be used for multichannel pipettes by adding a cell for each channel to be measured. Another reason for using a channel rather than pipetting into the cell entry port 53 of the cell 34 is that the required optical elements for a vertical absorbance measurement would be in the way of a pipette unless the cell 34 were moved out of the vertical light path. Although this is possible, it is desirable to minimize mechanical mechanisms to make a less expensive and more robust design.

With continuing reference to the method of the present invention, at the start of the first pipette calibration of the day, the system 10 empties the cell 34 and refills it with fresh diluent 37. It may be taken for granted that there will be some of each chromophore left in the cell. The exact amount will not be known until absorbance measurements are made. Complete flushing of the cell 34 at the start of each calibration is unnecessary and wasteful of the diluent 37. The cell 34 is filled to a certain approximate level (e.g. 2 ml) with diluent 37 at the start of the run, but it will of necessity have unknown concentrations of chromophores. We can only say that, prior to the steps described here, to the extent there is any residue of diluent, sample solution or a mixture thereof in the cell 34, the concentration of the second chromophore is likely to be relatively low and the concentration of the first chromophore will be less than that in the diluent 37.

At the start of a run, after the cell 34 has been filled, it contains concentration $C_1(0)$ of the first chromophore. The (0) indicates that this is the initial condition. It will be a (1) after the first sample solution addition (with attendant diluent flush) and so forth. It also contains concentration $C_2(0)$ of the second chromophore. The total volume of diluent and sample solution in the cell 34 is $V_T(0)$ and the height of the liquid contents in the cell 34 through which the vertical beam must pass is h(0). At the start of the calibration there are $M_1(0)$ moles of the first chromophore and $M_2(0)$ moles of the second chromophore. These quantities are unknown at the outset. As noted, the cell 34 has cross sectional area $S_c$, and a horizontal optical pathlength l. The values of $S_c$ and l may be different for each specific version of the system 10, but the values for the specific cell have been retained. The extinction coefficient of the first chromophore at wavelength 2 is $\epsilon_{1,2}$. The absorbance measured vertically at wavelength 1 after step 0 is $A_1^v(0)$ and the horizontal absorbance is $A_1^h(0)$.

The following relationships hold in general, no matter how many aliquots of sample solution have been added or how much diluent has been added:

Liquid Depth. The relationship between liquid depth in the cell 34 and the total volume of liquid contents in the cell 34 after the ith sample solution addition is:

$$V_T(i) = S_c h(i) - V_{mix} \quad (1.1)$$

If a mix bar is used as the mixing element 54 to mix the contents of the cell 34 then $V_{mix}$ is positive; if a recirculation loop is used as the mixing element 54 to mix then the volume of the recirculation loop is negative. It is possible that both forms of mixing could be used, in which case the two volumes might partially or fully offset each other. It is also possible to mix by sloshing or vortexing the cell contents without any mixing device present in the cell, in which case $V_{mix}=0$.

Total Volume of liquid in the cell 34. The vertical and horizontal absorbances at wavelength 1 after the $i^{th}$ sample solution addition are:

$$A_1^v(i) = C_1(i)\epsilon_{1,1}h(i) \quad (1.2)$$

$$A_1^h(i) = C_1(i)\epsilon_{1,1}l \quad (1.3)$$

Divide these two and solve for h(i):

$$h(i) = l\frac{A_1^v(i)}{A_1^h(i)} \quad (1.4)$$

Now put this result into equation (1.1)

$$V_T(i) = S_c l\frac{A_1^v(i)}{A_1^h(i)} - V_{mix} \quad (1.5)$$

This equation (1.5) allows a calculation of the total volume of liquid contents in the cell 34 at any step, based on known quantities ($S_c$, l and $V_{mix}$) and two measured absorbances. $A_1^v(i)$ and $A_1^h(i)$. We do not need to know anything about how much sample solution has been added versus how much of the diluent 37, and we do not need to know the concentration of the first chromophore in the diluent 37. It need only be concentrated enough so that the absorbance readings are in a range where the spectrophotometer subsystem 12 gives optimum performance, typically between 0.75 and 1.25 absorbance units.

Concentration of the second chromophore. Apply equation (1.3) to the second chromophore measured horizontally at wavelength 2:

$$A_2^h(i) = C_2(i)\epsilon_{2,2} \quad (1.6)$$

If the chromophore obeys Beer's law perfectly then the extinction coefficient $\epsilon_{2,2}$ will be constant. For very exacting quantitative work, it is common to observe a deviation from linearity; e.g., $\epsilon_{2,2}$ is not constant but depends on concentration. This dependence can be quantified in a well equipped laboratory, and an empirical relationship found which expresses the dependence of extinction coefficient as a function of concentration. For the purpose of this invention, the dependence is assumed to be well characterized allowing a relationship between concentration and extinction coefficient which can be expressed by means of a function with known coefficients (e.g. polynomial expansion). The coefficients can be measured in the manufacturing laboratory and passed to the instrument via a bar code on the reagent bottle or other means. The relationship between extinction coefficient and concentration is: $\epsilon_{2,2}(C_2(i))$.

Equation (1.6) now becomes $$A_2^h(i) = C_2(i)\epsilon_{2,2}(C_2(i)) \tag{1.7}$$

Given the measured absorbance, the known pathlength l, and the coefficients describing the dependence of extinction coefficient on concentration, this equation can be solved for concentration $C_2$ (i), if necessary by using successive approximations. In the calculations below, any time a concentration is referred to, it is the value resulting when equation (1.7) is used to calculate concentration using either an analytic expression or successive approximation.

After completing the initial characterization of the contents of the cell 34, the next step of the method is to add the sample solution to be analyzed. The cell 34 initially contains $M_2$ (0) moles of the second chromophore, left over from a previous operation. After the first aliquot of sample solution and a volume of flushing diluent 37 are added to and mixed into the existing contents of the cell 34 it contains $M_2$ (1) moles. The difference between $M_2$ (0) and $M_2$ (1) is the amount added in the first aliquot of sample solution (which has concentration $C_{S2}$ of the second chromophore):

$$M_2(1) = M_2(0) + V_S(1)C_{S2} \tag{1.8}$$

This is independent of the volume of diluent flush solution, because the diluent used for flushing contains none of the second chromophore. $C_{S2}$ is a value measured in the manufacturing lab for each specific lot of reagent, and passed to the system 10 via a bar code on the kit package, or by other means. Equation (1.8) can be solved for the sample volume $V_S$ (1):

$$V_S(1) = \frac{1}{C_{S2}}(M_2(1) - M_2(0)) \tag{1.9}$$

New horizontal and vertical measurements of absorbance at the first wavelength are taken and a new total volume $V_T(1)$ is calculated using equation (1.5). A horizontal absorbance measurement at the second wavelength together with equation (1.7) is then used to determine the new concentration $C_2$ (1) of the second chromophore. From these quantities and the definition of concentration we get:

$$V_S(1) = \frac{1}{C_{S2}}[C_2(1)V_T(1) - C_2(0)V_T(0)] \tag{1.10}$$

This relationship gives an exact value for sample solution volume based on results of two prior calculations (equations (1.5) and (1.7)) for the initial condition and the condition after addition of the first aliquot of sample solution. Equation (1.10) can be generalized to find the volume of any sample addition:

$$V_S(n) = \frac{1}{C_{S2}}[C_2(n)V_T(n) - C_2(n-1)V_T(n-1)] \tag{1.11}$$

Additional aliquots of the sample solution can be added to the cell 34 successively until one or more limits are reached, at which point the computer device processing the output information and/or controlling operation of the system 10 causes the cell 34 to emptied and refilled with a starting amount of the diluent 37.

When the absorbance at wavelength 2 has gotten to the end of its allowed range, or if the total volume will be too large after the next delivery, or if the number of data points in the run exceeds some preset limit, the system 10 will automatically drain the cell 34, recharge it with a fresh load of the diluent 37, and take the initial absorbance readings. The operator of the system 10 may then be prompted to add the next aliquot of sample solution. In this way, any number of data points can be taken for a pipette calibration of any volume less than the total capacity of the cell. The process of draining the cell 34, recharging it with the diluent 37, and taking the zero readings is fully automated.

The first time in a day that the system 10 is used it will flush the cell 34 with enough diluent 37 to assure that there is no second chromophore in the cell 34, and horizontal absorbance readings will be made at all wavelengths except the first one. This establishes the baseline for these wavelengths at the start of the day. The previously established relationship between baseline at wavelengths 1 and 2 will be applied, to infer to baseline for wavelength 1 readings. This baseline setting operation may also be automatically repeated any time that the ambient temperature changes by more than a pre-established amount from the initial baseline readings. This is done because the optical elements of the spectrophotometers may be temperature dependent, so without setting the baseline again the results could drift with temperature. An additional calibration step may be used on a periodic basis to confirm the correct operation of the system 10. The recommended calibration interval may be dependent on the stability of the system 10. Of course, a calibration may be performed at any time.

A calibration process of the present invention includes the following steps. First, a user of the system 10 replaces the diluent container 38 with one containing baseline solution, which is simply a clear non-absorbing solution. The system 10 automatically flushes the cell 34 with enough baseline solution to clear out any of the chromophores. The system 10 then takes both vertical and horizontal absorbance readings at all available wavelengths. These values are recorded for future use. The user is then prompted to use a pipette or other transfer device to add a special calibration solution which contains accurately known concentrations of both chromophores. The calibration solution will be added into the entry port 50. The system 10 will empty and call for more of the calibration solution and continue flushing until the cell 34 is filled with the calibration solution right up to the overflow port 58. At this time, the vertical pathlength is known to be equal to the height of that port 58. This height is denoted as h(C). This height should be established at the origin of the cell 34 and stored as indicated. Given the known values of h(C) and l from equation (1.4), the ratio of vertical to horizontal absorbances should be:

$$\frac{A_1^v(i)}{A_1^h(i)} = \frac{h(C)}{l} \qquad (1.12)$$

If the measured absorbance ratio is not equal to this ratio (or is outside of some predetermined tolerance) then the system 10 has failed this particular calibration test. The absolute value of the horizontal absorbance at each of the wavelengths should likewise be within some tolerance of the values given on the bar code on the bottle of calibration solution, as determined at the origin of the calibration solutions using instruments whose results are traceable to national standards. It may be desirable to have several different concentrations of calibration solution to test the absorbance accuracy at different levels. If so, the operator would calibrate the system 10 using each of the solutions in turn. Another option for instrument calibration is to use optical filters which may be moved in and out of the horizontal and vertical beams to attenuate them and calibrate the response of the spectrophotometers.

Other variations of the system 10 and methods described and shown herein can be implemented. Additionally, the processes, steps thereof and various examples and variations of these processes and steps, individually or in combination, may be implemented as a computer program product tangibly embodied as computer-readable signals on a computer-readable medium, for example, a non-volatile recording medium, an integrated circuit memory element, a distinct database, or a combination thereof. Such a computer program product may include computer-readable signals tangibly embodied on the computer-readable medium, where such signals define instructions, for example, as part of one or more programs that, as a result of being executed by a computer, instruct the computer to perform one or more processes or acts described herein, and/or various examples, variations and combinations thereof. Such instructions may be written in any of a plurality of programming languages, for example, Java, Visual BASIC, XML, C, or C++, FORTRAN, Pascal, Eiffel, BASIC, COBOL, and the like, or any of a variety of combinations thereof. The computer program may be of the type provided by Artel, Inc., of Westbrook, Me., with its liquid delivery device test products.

It is to be understood that various modifications may be made to the system and/or the method as described herein without departing from the spirit and scope of the invention. Accordingly, other embodiments are within the scope of the claims appended hereto.

What is claimed is:

1. A system for determining the volume of a sample solution delivered to a cell by a liquid delivery device to aid in testing the liquid delivery device, the system comprising:
   a. a cell having a cell entry port arranged to receive the sample solution from the liquid delivery device into the cell, a substantially constant cross sectional area and a known horizontal optical pathlength and arranged to contain the liquid therein;
   b. a horizontal beam spectrophotometer arranged to transmit a horizontal optical beam through contents in the cell and to output information indicative of light absorbance by the contents, wherein the contents of the cell includes a diluent, wherein the diluent includes a first chromophore;
   c. a vertical beam spectrophotometer arranged to transmit a vertical optical beam through the contents in the cell and to output information indicative of light absorbance by the contents, wherein the contents in the cell includes the sample solution and the diluent, wherein the sample solution includes a second chromophore; and
   d. a computer program arranged to calculate the volume of the sample solution dispensed by the liquid delivery device into the cell based on the substantially constant cross sectional area, the known horizontal optical pathlength, the light absorbance information from the horizontal beam spectrophotometer and the light absorbance information from the vertical beam spectrophotometer.

2. The system of claim 1 further comprising a pump arranged to deliver the diluent to the cell through the cell entry port.

3. The system of claim 2 wherein the second chromophore of the sample solution has absorption characteristics distinct from absorption characteristics of the first chromophore of the diluent.

4. The system of claim 3 further comprising a set of reagent solutions having known optical properties including the diluent with an amount of the first chromophore and the sample solution having a known concentration of the second chromophore.

5. The system of claim 3 further comprising a mixing element to mix the diluent and the sample solution together.

6. The system of claim 1 wherein the cell includes an overflow port to prevent complete filling of the cell.

7. The system of claim 1 wherein the cell includes an opening at a top thereof to allow delivery of the sample solution into the cell and bypass the cell entry port.

8. A method for determining the volume of a sample solution delivered to a cell by a liquid delivery device to aid in testing the liquid delivery device, the method comprising the steps of:
   a. delivering a diluent to a cell, wherein the diluent includes a first chromophore and the cell includes a substantially constant cross sectional area and a known horizontal optical pathlength;
   b. detecting a first absorbance of the first chromophore in the cell using horizontal beam spectrophotometry and vertical beam spectrophotometry;
   c. delivering the sample solution to the cell using liquid delivery device, wherein the sample solution includes a second chromophore, the second chromophore having light absorption characteristics different from light absorption characteristics of the first chromophore;
   d. detecting a second absorbance of the first chromophore in the cell using horizontal beam spectrophotometry and vertical beam spectrophotometry;
   e. detecting an absorbance of the second chromophore in the cell using horizontal beam spectrophotometry; and
   f. determining the volume of the sample solution delivered by the liquid delivery device into the cell using the substantially constant cross sectional area, the known horizontal optical pathlength and the absorbances detected.

9. The method of claim 8 further comprising the step of repeating steps c.-f. one or more times.

10. The method of claim 8 further comprising the step of mixing the diluent and the sample solution together in the cell to make a diluent-sample solution mixture prior to detecting the second absorbance of the first chromophore.

11. The method of claim 10 further comprising the step of removing the diluent-sample solution mixture after the step of determining the volume of the sample solution delivered.

12. The method of claim 11 further comprising the step of repeating steps c.-f. one or more times.

13. The method of claim 8 further comprising the step of determining a volume of the diluent in the cell prior to delivering the sample solution to the cell.

14. The method of claim 13 wherein the step of determining the volume of the diluent includes using the equation $$V_T(i) = S_c l \frac{A_1^v(i)}{A_1^h(i)} - V_{mix},$$

wherein $V_T$ is the volume of diluent and any remaining fluid in the cell, $S_c$ is the substantially constant cross sectional area of the cell, l is the known horizontal optical pathlength of the cell, $A_1^v$ is the absorbance of the first chromophore detected by the vertical beam spectrophotometry, $A_1^h$ is the absorbance of the first chromophore detected by the horizontal beam spectrophotometry and $V_{mix}$ is any volume within the cell taken up by any mixing element that may be in the cell.

15. The method of claim 14 wherein the step of determining the volume of the sample solution delivered to the cell by the liquid delivery device includes using the equation $$V_S(1) = \frac{1}{C_{S2}}[C_2(1)V_T(1) - C_2(0)V_T(0)],$$

wherein $C_{s2}$ is a known of the second chromophore contained in the sample solution.

16. The method of claim 13 further comprising the step of determining a concentration of the second chromophore in the cell is determined by using the equation $A_2^h(i) = C_2(i)\epsilon_{2,2}(C_2(i))$ and solving for the concentration $C_2(i)$ using the known relationship between extinction coefficient and concentration which has been passed to the system via a bar code or other means.

* * * * *